US010485840B1

(12) United States Patent
Jung

(10) Patent No.: US 10,485,840 B1
(45) Date of Patent: Nov. 26, 2019

(54) METHOD FOR PREPARING FUNCTIONAL HEALTH FOOD COMPRISING ALOESWOOD FOR PROMOTING MEMORY AND PERCEPTIVITY

(71) Applicant: Jong Moon Jung, Seoul (KR)

(72) Inventor: Jong Moon Jung, Seoul (KR)

( * ) Notice: Subject to any disclaimer, the term of this patent is extended or adjusted under 35 U.S.C. 154(b) by 0 days.

(21) Appl. No.: 16/517,644

(22) Filed: Jul. 21, 2019

(30) Foreign Application Priority Data

Dec. 26, 2018 (KR) .......................... 10-2018-0169728

(51) Int. Cl.
| | |
|---|---|
| *A61K 36/00* | (2006.01) |
| *A61K 36/835* | (2006.01) |
| *A61K 36/52* | (2006.01) |
| *A61K 36/16* | (2006.01) |
| *A61K 36/185* | (2006.01) |
| *A61K 35/62* | (2006.01) |
| *A61K 35/644* | (2015.01) |
| *A61K 36/815* | (2006.01) |
| *A61K 36/232* | (2006.01) |
| *A61K 36/78* | (2006.01) |
| *A61K 36/288* | (2006.01) |
| *A61K 36/53* | (2006.01) |
| *A61K 36/40* | (2006.01) |

(52) U.S. Cl.
CPC ............ *A61K 36/835* (2013.01); *A61K 35/62* (2013.01); *A61K 35/644* (2013.01); *A61K 36/00* (2013.01); *A61K 36/16* (2013.01); *A61K 36/185* (2013.01); *A61K 36/232* (2013.01); *A61K 36/288* (2013.01); *A61K 36/40* (2013.01); *A61K 36/52* (2013.01); *A61K 36/53* (2013.01); *A61K 36/78* (2013.01); *A61K 36/815* (2013.01)

(58) Field of Classification Search
None
See application file for complete search history.

(56) References Cited

U.S. PATENT DOCUMENTS

| | | | |
|---|---|---|---|
| 4,631,286 A | 12/1986 | Shutske et al. | |
| 4,639,468 A | 1/1987 | Roncucci et al. | |
| 4,753,950 A | 6/1988 | Shutske et al. | |
| 5,391,553 A | 2/1995 | Shutske et al. | |
| 5,401,749 A | 3/1995 | Shutske et al. | |
| 9,115,334 B2 | 8/2015 | Hur et al. | |
| 2009/0068291 A1* | 3/2009 | Cyr .......................... | A61K 8/97 424/725 |

FOREIGN PATENT DOCUMENTS

| | | |
|---|---|---|
| EP | 0 268 871 A1 | 6/1988 |
| JP | S61-148154 A | 7/1986 |
| JP | S63-141980 A | 6/1988 |
| JP | S63-166881 A | 7/1988 |
| JP | S63-203664 A | 8/1988 |
| JP | S63-225358 A | 9/1988 |
| JP | S63-238063 A | 10/1988 |
| JP | S63-239271 A | 10/1988 |
| JP | 2000-325040 A | 11/2000 |
| KR | 10-2011-0122640 A | 11/2011 |
| KR | 10-1751398 B1 | 6/2017 |
| KR | 10-2018-0036401 A | 4/2018 |
| WO | 88/02256 A1 | 4/1988 |

* cited by examiner

*Primary Examiner* — Qiuwen Mi
(74) *Attorney, Agent, or Firm* — Im IP Law; C. Andrew Im; Chai Im

(57) ABSTRACT

A method for preparing a functional health food including 40-60 parts by weight of *Huperzia serrata* powder, 90-110 parts by weight of walnut powder, 90-110 parts by weight of *Ginkgo biloba* leaf powder, 90-110 parts by weight of lotus root powder, 40-60 parts by weight of vegetable worm powder, 40-60 parts by weight of *Corni fructus* powder, 90-110 parts by weight of *lycium* Chinese powder, and 90-110 parts by weight of puer tea powder. The functional health food further includes 90-110 parts by weight of Korean *angelica* root powder, 40-60 parts by weight of *Saururus chinensis* (Lour.) baill powder, 40-60 parts by weight of white-flowering Korean dandelion powder, 40-60 parts by weight of *perilla* powder, and 2,500-3,500 parts by weight of honey on the basis of 100 parts by weight of aloeswood powder.

2 Claims, No Drawings

METHOD FOR PREPARING FUNCTIONAL HEALTH FOOD COMPRISING ALOESWOOD FOR PROMOTING MEMORY AND PERCEPTIVITY

RELATED APPLICATION

The present application claims priority from Korean Patent Application No. 10-2018-0169728 filed Dec. 26, 2018, which are incorporated herein by reference in its entirety.

FIELD OF THE INVENTION

The present invention relates to a functional health food having aloeswood for promoting memory and perceptivity and a preparation method thereof, and more particularly, to a functional health food having aloeswood for promoting memory and perceptivity and a preparation method thereof that are capable of promoting memory and/or perceptivity of a human being to prevent diseases like dementia.

BACKGROUND OF THE RELATED ART

Memory is the ability to remember the past in a conscious or unconscious state, and since learning and memory are closely connected with each other, especially, they should be always considered together.

The memory is divided into unconscious non-declarative memory including acquirement of techniques, habits, and so on and declarative memory including facts or events in the past, which can be reproduced consciously.

If complicate activities like driving, playing the piano, and the like become habituated, however, they can be carried out unconsciously, and through the repeated activities, therefore, the declarative memory can be converted into the non-declarative memory.

The declarative memory is classified into working memory collected to information given at the moment to allow the information to be temporarily stored only for several seconds, short-term memory kept for several hours to days, and remote memory capable of remembering past experiences a long time ago.

The short-term memory includes a term in which the memory on the event currently occurring is converted into the remote memory. During the term, the event is hard to be stored as memory and is easily forgotten, but only if the event is stored as the remote memory, it is not easily forgotten even in a case where serious injury happens to the brain.

As social environments are diversified, on the other hand, people are exposed to a lot of stimuli so that rapid brain activities are required to receive such stimuli.

Particularly, environment destruction, water pollution, and overflow of instant foods, which are caused by economic growth and industrialization, threaten health of people, and over-nutrition of meat eating caused by income increase and absolute lack of exercise caused by the development of machines accelerate obesity of people. Due to the obesity, further, chronic degenerative adult diseases such as arteriosclerosis, hypertension, coronary heart diseases, myocardial infarction, angina pectoris, cerebral infarction, and the like have been prevailed.

Also, patients with Alzheimer-type dementia have been increased every year. Further, the youth, especially, examinees feel fatigued in brain, mind and body because of their learning activity for long term, and such fatigue gives serious influences on healthy development of brain.

As the society is complicated and college entrance examination competition is fierce, accordingly, there is a definite need for developing a method for cleaning brain to promote memory and to accelerate fatigue recovery.

So as to satisfy such need, up to now, there have been proposed various treatments and conditions related to memory for the purpose of memory disorder treatment, memory promotion, or brain function activation.

For example, it is suggested that memory disorders are connected with aging process or neurodegenerative diseases like Alzheimer's disease and also memory deficits happen after brain injury or multi-infarct dementia.

Many chemical compounds and treatment methods have been studied to improve perception, that is, to promote memory and to store the memory for long term. As compounds useful in promotion of memory and treatment of memory disorders, for example, Milacemide (U.S. Pat. No. 4,639,468) have been developed.

Further, as a treatment method for various memory disorders like Alzheimer's disease having decreased cholinergic nerve functions, acetylcholin esterase inhibitor is used to increase contents of acetylcholin.

Also, a specific 9-amino-tetrahydroacridine derivative has an effect of inhibiting acetylcholin esterase so that it is effective in treatment of Alzheimer's disease (Japanese Patent Nos. S61-148154, S63-141980, S63-166881, S63-203664, S63-225358, S63-238063 and S63-239271, European Patent No. EP0268871A1, and International Patent No. WO88/02256).

However, the treatment for the Alzheimer's disease is not sufficiently achieved with the above-mentioned methods, and also, additional processes have to be required to produce the compounds massively. If the compounds are applied to the living body, toxicity may be generated from the compounds.

So as to overcome such problems, up to now, medicines or functional health foods to which prescription for oriental medicine is partially applied have been developed to achieve memory promotion and brain function activation.

The most representatively emerging food is *Panax ginseng* C.A. Meyer among them, and up to now, many studies have been made on the effects of *ginseng* on brain activities like learning, memory, and so on.

In addition to *ginseng*, blue-backed fish, especially, head of tuna contains a large amount of docosahexaenoic acid (DHA), and recently, it is widely known that the DHA is important for the development of the brain, which becomes a global issue. Accordingly, many studies on the DHA have been made.

According to the study, the DHA has a memory and learning control function through memory and learning tests and is very effective in prevention of Alzheimer-type dementia. However, it is known that the DHA is important for the development of the brain only in infants and gives no influence on the development of the brain or the improvement of memory in growing children or adults. Above all, the DHA has to be extracted from tuna, and even if it is artificially synthesized, an appropriate process for mass production has to be required, which raises a manufacturing cost and undesirably giving no economical advantages.

Under the above-mentioned situation, there is a need for the development of desirable natural medicines having effects on the promotion of memory and learning ability to which much attention in modern societies is paid, and especially, there is a definite need for the development of a functional health food which is prepared with non-toxic and economical natural components, thereby being contributed to the industrialization of natural resources and being easily accessed to demanders.

SUMMARY OF THE INVENTION

Accordingly, the present invention has been made in view of the above-mentioned problems occurring in the prior art, and it is an object of the present invention to provide a functional health food having aloeswood for promoting memory and perceptivity and a preparation method thereof that are capable of having effects of promoting learning ability and memory, improving various memory impairment due to aging, and preventing and treating dementia.

To accomplish the above-mentioned object, according to one aspect of the present invention, there is provided a functional health food including 40 to 60 parts by weight of *Huperzia serrata* powder, 90 to 110 parts by weight of walnut powder, 90 to 110 parts by weight of *Ginkgo biloba* leaf powder, 90 to 110 parts by weight of lotus root powder, 40 to 60 parts by weight of vegetable worm powder, 40 to 60 parts by weight of *Corni fructus* powder, 90 to 110 parts by weight of *lycium* Chinese powder, 90 to 110 parts by weight of puer tea powder, 90 to 110 parts by weight of Korean *angelica* root powder, 40 to 60 parts by weight of *Saururus chinensis* (Lour.) baill powder, 40 to 60 parts by weight of white-flowering Korean dandelion powder, 40 to 60 parts by weight of *perilla* powder, and 2,500 to 3,500 parts by weight of honey on the basis of 100 parts by weight of aloeswood powder.

To accomplish the above-mentioned object, according to other aspect of the present invention, there is provided a method for preparing a functional health food, including the steps of: washing aloeswood, *Huperzia serrata*, walnuts, *Ginkgo biloba* leaves, lotus roots, vegetable worms, *Corni fructus*, *lycium* Chinese, puer tea, Korean *angelica* roots, *Saururus chinensis* (Lour.) baill, white-flowering Korean dandelion, and *perilla* with water and drying the washed materials in a shade; grinding the respective dried materials by means of a grinding mill to the form of powder; steaming the respective powdered materials in a big pot heated to a temperature of 90 to 120° C. for one to second minutes and cooling the respective steamed materials to allow the respective materials to be sterilized and flavored; sealing a mixture made by mixing 40 to 60 parts by weight of the *Huperzia serrata* powder, 90 to 110 parts by weight of the walnut powder, 90 to 110 parts by weight of the *Ginkgo biloba* leaf powder, 90 to 110 parts by weight of the lotus root powder, 40 to 60 parts by weight of the vegetable worm powder, 40 to 60 parts by weight of the *Corni fructus* powder, 90 to 110 parts by weight of the *lycium* Chinese powder, 90 to 110 parts by weight of the puer tea powder, 90 to 110 parts by weight of the Korean *angelica* root powder, 40 to 60 parts by weight of the *Saururus chinensis* (Lour.) baill powder, 40 to 60 parts by weight of the white-flowering Korean dandelion powder, and 40 to 60 parts by weight of the *perilla* powder on the basis of 100 parts by weight of the aloeswood powder and maturing the sealed mixture for six to eight days; pouring natural water larger by one to three times than the mixture with respect to the total weight of the mixture to the mixture whose maturing is finished and boiling the mixture at a temperature in a range of 90 to 98° C. for five to 20 minutes; cooling and drying the mixture at an ambient temperature; and mixing the mixture with 2,500 to 3,500 parts by weight of honey on the basis of 100 parts by weight of the aloeswood.

DETAILED DESCRIPTION OF THE EMBODIMENTS

Now, the present invention will be in detail explained.

According to one aspect of the present invention, the present invention provides a functional health food comprising 40 to 60 parts by weight of *Huperzia serrata* powder, 90 to 110 parts by weight of walnut powder, 90 to 110 parts by weight of *Ginkgo biloba* leaf powder, 90 to 110 parts by weight of lotus root powder, 40 to 60 parts by weight of vegetable worm powder, 40 to 60 parts by weight of *Corni fructus* powder, 90 to 110 parts by weight of *lycium* Chinese powder, 90 to 110 parts by weight of puer tea powder, 90 to 110 parts by weight of Korean *angelica* root powder, 40 to 60 parts by weight of *Saururus chinensis* (Lour.) baill powder, 40 to 60 parts by weight of white-flowering Korean dandelion powder, 40 to 60 parts by weight of *perilla* powder, and 2,500 to 3,500 parts by weight of honey on the basis of 100 parts by weight of aloeswood powder.

According to other aspect of the present invention, the present invention provides a method for preparing a functional health food, comprising the steps of: washing aloeswood, *Huperzia serrata*, walnuts, *Ginkgo biloba* leaves, lotus roots, vegetable worms, *Corni fructus, lycium* Chinese, puer tea, Korean *angelica* roots, *Saururus chinensis* (Lour.) baill, white-flowering Korean dandelion, and *perilla* with water and drying the washed materials in a shade; grinding the respective dried materials by means of a grinding mill to the form of powder; steaming the respective powdered materials in a big pot heated to a temperature of 90 to 120° C. for one to second minutes and cooling the respective steamed materials to allow the respective materials to be sterilized and flavored; sealing a mixture made by mixing 40 to 60 parts by weight of the *Huperzia serrata* powder, 90 to 110 parts by weight of the walnut powder, 90 to 110 parts by weight of the *Ginkgo biloba* leaf powder, 90 to 110 parts by weight of the lotus root powder, 40 to 60 parts by weight of the vegetable worm powder, 40 to 60 parts by weight of the *Corni fructus* powder, 90 to 110 parts by weight of the *lycium* Chinese powder, 90 to 110 parts by weight of the puer tea powder, 90 to 110 parts by weight of the Korean *angelica* root powder, 40 to 60 parts by weight of the *Saururus chinensis* (Lour.) baill powder, 40 to 60 parts by weight of the white-flowering Korean dandelion powder, and 40 to 60 parts by weight of the *perilla* powder on the basis of 100 parts by weight of the aloeswood powder and maturing the sealed mixture for six to eight days; pouring natural water larger by one to three times than the mixture with respect to the total weight of the mixture to the mixture whose maturing is finished and boiling the mixture at a temperature in a range of 90 to 98° C. for five to 20 minutes; cooling and drying the mixture at an ambient temperature; and mixing the mixture with 2,500 to 3,500 parts by weight of honey on the basis of 100 parts by weight of aloeswood.

According to the present invention, aloeswood (*Aquilaria crassna*) powder is obtained by powdering aloeswood produced from aloeswood trees, and only if the aloeswood powder is general aloeswood powder as appreciated in this art, all kinds of aloeswood powder can be freely used.

Especially, the aloeswood powder comprises Agarospirol giving effects of releasing a central nervous system and clearing the head, Agarofuran giving an effect of stabilizing the central nervous system, Terpineol giving an effect of anticonvulsant, and Dehydrofukinone giving an effect of stabilizing the central nervous system, and further, the aloeswood powder has an antibacterial effect, an effect of releasing brain-stabilizing central nerves in the central nervous system, and an effect of cleaning the brain to improve memory and/or perceptivity.

According to the present invention, the functional health food having aloeswood for promoting memory and perceptivity is characterized in that the contents of all components except the aloeswood powder are determined on the basis of 100 parts by weight of the aloeswood powder.

According to the present invention, the *Huperzia serrata* powder is obtained by powdering *Huperzia serrata*.

In this case, the *Huperzia serrata* is a medicine that has been used for a long history, has been introduced in various kinds of medical research in China and so on, and has anti-acetylcholinesterase properties.

At this time, the anti-acetylcholinesterase has an effect of dementia treatment and prevention from 1980s, and thus, it has been widely used over the world. In addition, the anti-acetylcholinesterase is used to treat Alzheimer's disease in China, and it is recently known that it helpfully promotes the perceptivity of a human being.

Moreover, recently, a herbal medicine laboratory in France has tried to obtain the *Huperzia serrata* produced in Vietnam so as to use the *Huperzia serrata* as a medicine for dementia treatment and prevention.

The contents of the *Huperzia serrata* powder are changeable according to a user's selection, but desirably, 40 to 60 parts by weight of the *Huperzia serrata* powder is mixed with respect to 100 parts by weight of the aloeswood powder.

According to the present invention, the walnut powder is obtained by powdering walnuts.

The walnuts are abundant in unsaturated fatty acids, and especially, they are good food materials for brain health and skin aging prevention, which is known well to various pharmacopoeias like "Donguibogam" and to people long ago.

Especially, the fatty acids and vitamin E abundantly contained in the walnuts have an anti-oxidant effect and serve to supply nutrition to the brain, and the walnuts comprise all kinds of vitamins (A, B1, B2, B6, C and E) as main ingredients and a variety of other ingredients, so that they are balanced well with all kinds of foods or medical herbs to allow the foods or medical herbs to take their advantages.

Desirably, 90 to 110 parts by weight of the walnut powder is mixed with respect to 100 parts by weight of the aloeswood powder.

According to the present invention, the *Ginkgo biloba* leaf powder is obtained by powdering *Ginkgo biloba* leaves and/or *Ginkgo biloba* leaf extract.

In this case, if the *Ginkgo biloba* leaf extract is a general *Ginkgo biloba* leaf extract in the art, all kinds of *Ginkgo biloba* leaf extracts may be freely used, but desirably, the *Ginkgo biloba* leaf extract is obtained by extracting the *Ginkgo biloba* leaves by means of alcohol or by means of distillation and/or pressurization.

On the other hand, the *Ginkgo biloba* leaves are the leaves of the most commonly landscape trees in Korea and serve to allow blood to be clean and to prevent memory reduction, that is, to improve memory and perceptivity, which is widely known long ago.

The contents of the *Ginkgo biloba* leaf powder are changeable according to a user's selection, but desirably, 90 to 110 parts by weight of the *Ginkgo biloba* leaf powder is mixed with respect to 100 parts by weight of the aloeswood powder.

According to the present invention, the lotus root powder is obtained by powdering lotus roots.

The lotus roots have been used as a food for the purpose of a medicine long ago and give effects of fatigue recovery, skin wrinkle improvement, and stabilization of insomnia symptoms and neurosis.

According to research results in Japan, recently, the lotus roots contain asparagines, arginine, thyroxine, amino acids and various kinds of vitamins as components for improving and promoting memory so that they can prevent brain cell aging and improve memory reduction (slipping moments). As a result, the lotus roots are developed to a shape of 'gum' and are easily purchased by everyone at convenience stores.

Desirably, 90 to 110 parts by weight of the lotus root powder is mixed with respect to 100 parts by weight of the aloeswood powder.

According to the present invention, the vegetable worm powder is obtained by powdering vegetable worms.

The vegetable worms are healthy foods produced in a high-altitude area of China and in Tibet at an altitude of 4,000 m or more and provide the best medical effects.

Desirably, 40 to 60 parts by weight of the vegetable worm powder is mixed with respect to 100 parts by weight of the aloeswood powder.

According to the present invention, the *Corni fructus* powder is obtained by powdering *Corni fructus*, and the *Corni fructus* serves to increase the strength of the human body and immunity.

The contents of the *Corni fructus* powder are changeable according to a user's selection, but desirably, 40 to 60 parts by weight of the *Corni fructus* powder is mixed with respect to 100 parts by weight of the aloeswood powder.

According to the present invention, the *lycium* Chinese powder is obtained by powdering *lycium* Chinese, and desirably, 90 to 110 parts by weight of the *lycium* Chinese powder is mixed with respect to 100 parts by weight of the aloeswood powder.

In this case, the *lycium* Chinese is good for improving concentration, memory, and learning ability and absorbs and dissolves fat to give diet effects.

According to the present invention, the puer tea powder is obtained by powdering puer tea, and if the puer tea powder is a general puer tea powder in the art, all kinds of puer tea powder may be freely used.

Desirably, 90 to 110 parts by weight of the puer tea powder is mixed with respect to 100 parts by weight of the aloeswood powder.

According to the present invention, the Korean *angelica* root powder is obtained by powdering Korean *angelica* roots, and the Korean *angelica* roots have strengthening effects and blood-cleaning effects.

The contents of the Korean *angelica* root powder are changeable according to a user's selection, but desirably, 90 to 110 parts by weight of the Korean *angelica* root powder is mixed with respect to 100 parts by weight of the aloeswood powder.

According to the present invention, the *Saururus chinensis* (Lour.) baill powder is obtained by powdering *Saururus chinensis* (Lour.) baill, is good for the bronchi, and has anti-oxidant and anti-inflammatory effects. Desirably, 40 to 60 parts by weight of the *Saururus chinensis* (Lour.) baill powder is mixed with respect to 100 parts by weight of the aloeswood powder.

According to the present invention, the white-flowering Korean dandelion powder is obtained by powdering white-flowering Korean dandelion and is good for improving anti cancer effects and renal functions.

Desirably, 40 to 60 parts by weight of the white-flowering Korean dandelion powder is mixed with respect to 100 parts by weight of the aloeswood powder.

According to the present invention, the *perilla* powder is obtained by powdering *perilla*, and desirably, 40 to 60 parts by weight of the *perilla* powder is mixed with respect to 100 parts by weight of the aloeswood powder.

According to the present invention, if the honey is general honey in the art, all kinds of honey may be freely used.

Desirably, 2,500 to 3,500 parts by weight of honey is mixed with respect to 100 parts by weight of aloeswood powder.

On the other hand, the powder among the components constituting the functional health food according to the present invention is produced by means of a powdering method generally used in the art, for example, ball milling.

According to the present invention, the functional health food having aloeswood for promoting memory and perceptivity further comprises one or more additives among specific additives as will be discussed below.

According to one aspect of the present invention, the functional health food according to the present invention further comprises 1 to 20 parts by weight of *Rehmannia glutinosa* powder with respect to 100 parts by weight of the aloeswood powder.

At this time, the *Rehmannia glutinosa* powder is obtained by drying and powdering *Rehmannia glutinosa*.

The *Rehmannia glutinosa* is a plant belonging to the family Scrophulariaceae, that is, a herbaceous perennial plant belonging to the family Phrymaleptostachya, originated from China, and commonly, has a root form. The *Rehmannia glutinosa* roots dug out in autumn are thick and long like small sweet potatoes and are thus gnarled.

The *Rehmannia glutinosa* comprises various useful chemical components such as iridoid, catalposide, acteoside, martynosides, and forsythiaside as irridoid glycoside, and phenolic glycosides. The components have effects of immune stimulation, blood sugar reduction, anti-aging, anti-gastric ulcer, gastric mucosa protection, anti-cancer, and gum strengthening. Further, the roots of the *Rehmannia glutinosa* contain large quantities of sugars like 6% of glucose, 32% of stachyose, and so on and 11 kinds of amino acids inclusive of arginine.

According to another aspect of the present invention, the functional health food according to the present invention further comprises 1 to 20 parts by weight of *Forsythiae fructus* powder with respect to 100 parts by weight of the aloeswood powder.

At this time, the *Forsythiae fructus* powder is obtained by drying and powdering *Forsythiae fructus*.

The *Forsythiae fructus* is a fruit of forsythia belonging to the family Oleaceae, which is taken at the time when it becomes first or fully ripe and is then dried by exposure to the sun.

Especially, the *Forsythiae fructus* is much used in oriental medicines as a fever reducer, an antidote, drainage, anti-inflammation, and diuretics, and also, it is used with other medical materials for treating pyogenic diseases, swelling, gonococcal infection, dysmenorrhea, diuresis, hemorrhoids, tuberculosis, scabies, and antidote. Extracts or dissolved materials of the fruit shells have an anti-bacterial effect, and flowers thereof contain quercetin glycoside, rutin, and ascorbic acids as pigment glycosides to give good anti-oxidative, anti-bacterial, anti-inflammatory, and elastase inhibiting effects as well as good effects for beauty.

Accordingly, the *Forsythiae fructus* has an excellent tyrosinase activation suppression effect and an excellent melanin production suppression effect to provide an amazing whitening effect.

According to yet another aspect of the present invention, the functional health food according to the present invention further comprises 1 to 20 parts by weight of *Coptis japonica* Makino powder with respect to 100 parts by weight of the aloeswood powder.

At this time, the *Coptis japonica* Makino powder is obtained by drying and powdering *Coptis japonica* Makino.

The *Coptis japonica* Makino is a perennial plant belonging to the family Ranunculaceae and has continuous yellow roots, which is called *Jeffersonia dubia* by villagers. The leaf thereof has a shape of an egg or triangle and is divided like feather. The *Coptis japonica* Makino grows on high mountains like Sichuan, Hubei, Guizhou, and Shaanxi in central part of China, or it is cultivated as a medical plant thereon.

The *Coptis japonica* Makino roots contain berberine and alkaloid so that they are used for yellow, especially, golden color dyeing, but the berberine has effects of blood pressure reduction, heart strengthening, fever reduction, bacterial suppression, release, and anti-inflammation, while also killing dermatophytes or white *candida* abicans. Further, the roots and stems of the *Coptis japonica* Makino are used as sedative and an anti-inflammatory agent to treat hyperemia, inflammatory diseases, palpitation, mental anxiety, stomachache, diarrhea, and dysentery.

According to still another aspect of the present invention, the functional health food according to the present invention further comprises 1 to 10 parts by weight of mugwort powder with respect to 100 parts by weight of the aloeswood powder.

At this time, the mugwort powder is obtained by drying and powdering mugwort.

The mugwort is a plant belonging to the family Asteraceae and has large contents of inorganic matters and vitamins, especially, vitamins A and C. The mugwort has effects of fever reduction, anti-bacteria, stomachache treatment, women's disease treatment, homeostasis, astringent activity, aging prevention, and heart disease treatment.

According to another aspect of the present invention, the functional health food according to the present invention further comprises 1 to 10 parts by weight of jellyfish powder with respect to 100 parts by weight of the Aloeswood powder.

At this time, the jellyfish powder is obtained by drying and powdering jellyfish.

The jellyfish contains large amounts of water, protein, fat, carbohydrate, and calcium and does not have any toxicity and adverse reaction even if it is used for long time, so that it is good for an initial hypertension patient. Further, the jellyfish has effects of neutral stability and constipation.

According to yet another aspect of the present invention, the functional health food according to the present invention further comprises 1 to 10 parts by weight of sea tangle powder with respect to 100 parts by weight of the aloeswood powder.

At this time, the sea tangle powder is obtained by drying and powdering sea tangle.

The sea tangle serves to lower a cholesterol value and a blood pressure, to lower a blood sugar value for the treatment of diabetes, to prevent a thyroid disease, to help bowel movement for the treatment of constipation, to discharge carcinogen, to strengthen bones and teeth, to remove hangover, and to prevent liver diseases.

According to still another aspect of the present invention, the functional health food according to the present invention further comprises 1 to 5 parts by weight of octopus powder with respect to 100 parts by weight of the aloeswood powder.

At this time, the octopus powder is obtained by drying and powdering octopus.

The octopus has a large amount of taurine to lower cholesterol and gives effects of sight recovery and anemia prevention.

According to yet still another aspect of the present invention, the functional health food according to the present invention further comprises 1 to 5 parts by weight of pumpkin powder with respect to 100 parts by weight of the aloeswood powder.

At this time, the pumpkin powder is obtained by drying and powdering pumpkin.

The pumpkin contains large amounts of dietary fibers, protein, mineral, vitamins A, C and E, and carbohydrate and lowers anti-diuretic hormone released from the human body to improve diuretic action. Further, the pumpkin has an excellent effect of anti-cancer to prevent cancer by means of carotene, improves digestion and absorption by means of carbohydrate, and has an excellent effect of swelling removal.

According to another aspect of the present invention, the functional health food according to the present invention further comprises 1 to 10 parts by weight of *Houttuynia cordata* powder with respect to 100 parts by weight of the aloeswood powder.

At this time, the *Houttuynia cordata* powder is obtained by drying and powdering *Houttuynia cordata*.

The *Houttuynia cordata* has an excellent effect on inside diseases caused by toxic heat, has effects on lung and bowl diseases, contains decontamination components to help clean skin management, and removes bad waste from the body to suppress the development of arteriosclerosis.

According to still another aspect of the present invention, the functional health food according to the present invention further comprises 1 to 10 parts by weight of jujube powder with respect to 100 parts by weight of the aloeswood powder.

At this time, the jujube powder is obtained by drying and powdering jujubes.

The jujubes have a large amount of sugar such as galactose, sucrose, maltose, and so on, and the sugar taste relaxes tension to give releasing and has an effect of nerve relaxation, so that if someone sleeps badly at night or dreams a lot, the jujubes are effective. Further, the jujubes serve to release postmenopausal women's symptoms of hysteria such as irritation, depression, and the like.

According to yet another aspect of the present invention, the functional health food according to the present invention further comprises 1 to 5 parts by weight of Chinese pea tree powder with respect to 100 parts by weight of the aloeswood powder.

At this time, the Chinese pea tree powder is obtained by drying and powdering Chinese pea tree.

The Chinese pea tree has a scientific name of *Caragana chamlagu* Lam and is a deciduous shrub having a height of 1 to 2 m, a stem straightly spread or collected in plural, thin and long leaves. Further, the Chinese pea tree has flowering time in May and fruiting time in September and October and is distributed in central and south districts, and a root thereof is called *Caragan sinica* root.

The *Caragan sinica* root is dug out any time all year around and is washed to remove mud therefrom. Next, fibrous roots and a dark and brown shell are peeled off and a fresh root is dried by exposure to the sun. The *Caragan sinica* root tastes bitter and sour and has calming properties. The root contains glycoalkaloids, saponin, and so on, which are transferred to central nerves to give an effect of blood pressure lowering. Further, the root has effects of lung-heat clearing, blood circulation smoothing, blood vessel communicating and thus treats deficiency and febrile symptoms, hypertension, and so on.

According to still another aspect of the present invention, the functional health food according to the present invention further comprises 1 to 5 parts by weight of green tea powder with respect to 100 parts by weight of the aloeswood powder.

At this time, the green tea powder is obtained by drying and powdering green tea.

The green tea serves to expand a blood vessel to lower serum lipid concentration or to lower an incidence rate of arteriosclerosis, and it has an effect of awakening to enhance metal activities, memory, and judgment. Also, the green tea suppresses headache, raises heart movement, and enhances diuretic action.

According to still another aspect of the present invention, the functional health food according to the present invention further comprises 1 to 5 parts by weight of turmeric powder with respect to 100 parts by weight of the aloeswood powder.

At this time, the turmeric powder is obtained by drying and powdering turmeric.

The turmeric is a perennial plant belonging to the family Zingiberaceae and contains curcumin to have effects of anti-oxidant, anti-inflammation, liver function improvement, and so on.

According to still another aspect of the present invention, the functional health food according to the present invention further comprises 1 to 5 parts by weight of *Orostachys japonica* powder with respect to 100 parts by weight of the aloeswood powder.

At this time, the *Orostachys japonica* powder is obtained by drying and powdering *Orostachys japonica*.

The *Orostachys japonica* is a perennial herb belonging to the genus *Orostachys* of the family Sedum sarmentosum, is distributed in East Asia, and generally grows on rock of mountains. The *Orostachys japonica* is a succulent plant having thick leaves, and because it looks like pine leaves growing on rock, it calls a rock pine. Further, it looks like pine growing on tiles. The *Orostachys japonica* has excellent effects of anti-oxidant activity, hypertension, dementia, Alzheimer's disease, and diabetes.

According to still another aspect of the present invention, the functional health food according to the present invention further comprises 0.1 to 1 parts by weight of zinc oxide powder with respect to 100 parts by weight of the aloeswood powder.

Zinc oxide is a mineral having excellent effects of improving immunity functions and prostate and urinary bladder functions and is also a molecule for constituting insulin. Further, the zinc oxide serves to accelerate energy metabolism and has excellent effects of obesity alleviation, prostatic hypeplasia, stamina increase, and taste improvement.

On the other hand, the functional health food according to the present invention can be manufactured in a liquid, solid or powder form. If the functional health food is made in the solid form, particularly, it desirably has shapes of pills.

Under the above-mentioned components, next, a method for preparing the functional health food according to the present invention will be explained.

First, aloeswood, *Huperzia serrata*, walnuts, *Ginkgo biloba* leaves, lotus roots, vegetable worms, *Corni fructus*, *lycium* Chinese, puer tea, Korean *angelica* roots, *Saururus chinensis* (Lour.) baill, white-flowering Korean dandelion, and *perilla* are washed cleanly with water and the washed materials are dried in a shade.

Next, the respective dried materials are grounded by means of a grinding mill to the form of powder.

The respective powdered materials are steamed in a big pot heated to a temperature of 90 to 120° C. for one to second minutes and the steamed materials are cooled to allow the respective materials to be sterilized and flavored.

After that, a mixture made by mixing 40 to 60 parts by weight of the *Huperzia serrata* powder, 90 to 110 parts by weight of the walnut powder, 90 to 110 parts by weight of the *Ginkgo biloba* leaf powder, 90 to 110 parts by weight of the lotus root powder, 40 to 60 parts by weight of the vegetable worm powder, 40 to 60 parts by weight of the *Corni fructus* powder, 90 to 110 parts by weight of the *lycium* Chinese powder, 90 to 110 parts by weight of the puer tea powder, 90 to 110 parts by weight of the Korean *angelica* root powder, 40 to 60 parts by weight of the *Saururus chinensis* (Lour.) baill powder, 40 to 60 parts by weight of the white-flowering Korean dandelion powder, and 40 to 60 parts by weight of the *perilla* powder on the basis of 100 parts by weight of the aloeswood powder is sealed and the sealed mixture is matured for six to eight days.

Natural water larger by one to three times than the mixture with respect to the total weight of the mixture is poured to the mixture whose maturing is finished and the mixture is boiled at a temperature in a range of 90 to 98° C. for five to 20 minutes.

Next, the mixture is cooled and then dried at an ambient temperature.

Lastly, the mixture is mixed with 2,500 to 3,500 parts by weight of honey on the basis of 100 parts by weight of aloeswood.

In this case, at the step of grinding the respective dried materials to the form of powder, the materials are grounded through a general grinding mill, and particle sizes of the powder are discriminated by means of a mesh. Desirably, the particle sizes of the powder can be discriminated in a range of 0.5 to 5 mm.

According to the present invention, the method for preparing the functional health food further includes the step of, after the step of mixing the mixture with the honey, forming the mixture to a given size, desirably, to a shape of about 2 g of pill.

According to the present invention, the method for preparing the functional health food further includes the step of, after the step of grinding the respective dried materials to the form of powder, adding one enzyme selected from lipxygenase and hydroperoxide lyase to the respective powdered materials. In this case, 0.1 to 0.3 parts by weight of the enzyme is added to the 100 parts by weight of each material, and at this time, the enzyme selected from lipxygenase and hydroperoxide lyase serves to prevent peculiar flavors and tastes of the respective materials from being lost and to increase flavor components like aldehyde, ketone, and so on.

According to the present invention, the method for preparing the functional health food further includes the step of, after the step of steaming the respective powdered materials, injecting carbonic acid gas or nitrogen gas which is colorless, odorless, inert, and harmless to the human body into the steamed materials in a sealed space and preventing water from entering again tissues of the respective materials by means of the injected gas to avoid the decay of the materials.

Hereinafter, the present invention will be in detail explained by way of particular embodiments, but the embodiments are suggested to describe the present invention in detail. Therefore, it should be appreciated that the scope of the present invention is not limited by the embodiments.

Embodiment 1

Aloeswood, *Huperzia serrata*, walnuts, *Ginkgo biloba* leaves, lotus roots, vegetable worms, *Corni fructus*, *lycium* Chinese, puer tea, Korean *angelica* roots, *Saururus chinensis* (Lour.) baill, white-flowering Korean dandelion, and *perilla* powder were washed cleanly with water and the washed materials were dried in a shade. Next, the respective dried materials were grounded by means of a grinding mill to the form of powder having particle sizes of 0.5 to 5 mm.

Next, the respective powdered materials were steamed independently of each other in a big pot heated to a temperature of about 100° C. for one minute and the respective steamed materials were cooled.

After that, a mixture, which was made by mixing 100 g of the aloeswood powder, 50 g of the *Huperzia serrata* powder, 100 g of the walnut powder, 100 g of the *Ginkgo biloba* leaf powder, 100 g of the lotus root powder, 50 g of the vegetable worm powder, 50 g of the *Corni fructus* powder, 100 g of the *lycium* Chinese powder, 100 g of the puer tea powder, 100 g of the Korean *angelica* root powder, 50 g of the *Saururus chinensis* (Lour.) baill powder, 50 g of the white-flowering Korean dandelion powder, and 50 g of the *perilla* powder was sealed and the sealed mixture was matured for six days.

Natural water larger by two times than the mixture with respect to the total weight of the mixture was poured to the mixture whose maturing is finished and the mixture was boiled at a temperature of 95° C. for 10 minutes. Next, the mixture was cooled and dried at an ambient temperature.

Lastly, the mixture was mixed with 3,000 g of honey and was made to the shape of 2 g of pills.

Embodiment 2

This embodiment was carried out in the same manner as in Embodiment 1, except that 0.2 g of lipoxigenase was added to each of the materials grounded to the powder having particle sizes of 0.5 to 5 mm, each material has a weight of 100 g.

Embodiment 3

This embodiment was carried out in the same manner as in Embodiment 2, except that the respective steamed and cooled powdered materials were impregnated with nitrogen gas in 10 L of a sealed space at a temperature of 50° C. for 10 hours.

Embodiment 4

This embodiment was carried out in the same manner as in Embodiment 1, except that 10 g of *Rehmannia glutinosa* powder was added to the mixture matured.

Embodiment 5

This embodiment was carried out in the same manner as in Embodiment 1, except that 10 g of *Forsythiae fructus* powder was added to the mixture matured.

Embodiment 6

This embodiment was carried out in the same manner as in Embodiment 1, except that 10 g of *Coptis japonica* Makino powder was added to the mixture matured.

Embodiment 7

This embodiment was carried out in the same manner as in Embodiment 1, except that 5 g of mugwort powder was added to the mixture matured.

Embodiment 8

This embodiment was carried out in the same manner as in Embodiment 1, except that 5 g of jellyfish powder was added to the mixture matured.

Embodiment 9

This embodiment was carried out in the same manner as in Embodiment 1, except that 5 g of sea tangle powder was added to the mixture matured.

Embodiment 10

This embodiment was carried out in the same manner as in Embodiment 1, except that 3 g of octopus powder was added to the mixture matured.

Embodiment 11

This embodiment was carried out in the same manner as in Embodiment 1, except that 3 g of pumpkin powder was added to the mixture matured.

Embodiment 12

This embodiment was carried out in the same manner as in Embodiment 1, except that 5 g of *Houttuynia cordata* powder was added to the mixture matured.

Embodiment 13

This embodiment was carried out in the same manner as in Embodiment 1, except that 5 g of jujube powder was added to the mixture matured.

Embodiment 14

This embodiment was carried out in the same manner as in Embodiment 1, except that 3 g of Chinese pea tree powder was added to the mixture matured.

Embodiment 15

This embodiment was carried out in the same manner as in Embodiment 1, except that 2 g of green tea powder was added to the mixture matured.

Embodiment 16

This embodiment was carried out in the same manner as in Embodiment 1, except that 3 g of turmeric powder was added to the mixture matured.

Embodiment 17

This embodiment was carried out in the same manner as in Embodiment 1, except that 3 g of *Orostachys japonica* powder was added to the mixture matured.

Embodiment 18

This embodiment was carried out in the same manner as in Embodiment 1, except that 0.5 g of zinc oxide powder was added to the mixture matured.

Embodiment 19

This embodiment was carried out in the same manner as in Embodiment 3, except that Embodiments 4 to 18 were carried out in this embodiment.

As described above, the functional health food and the preparation method thereof according to the present invention can effectively promote memory and learning ability of young children and youth, can improve various memory impairment caused by aging in stages of early old age and old age, and can be usefully used as an agent for preventing and treating dementia.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention. The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention.

What is claimed is:

1. A method for preparing a functional health food, comprising steps of:

washing aloeswood, *Huperzia serrata*, walnuts, *Ginkgo biloba* leaves, lotus roots, vegetable worms, *Corni fructus*, *lycium* Chinese, puer tea, Korean *angelica* roots, *Saururus chinensis* (Lour.) baill, white-flowering Korean dandelion, and *perilla* with water and drying the washed materials in a shade;

grinding the respective dried materials using a grinding mill to the form of powder;

steaming the respective powdered materials in a pot heated to a temperature of 90 to 120° C. for one to two minutes and cooling the respective steamed materials to allow the respective materials to be sterilized and flavored;

sealing a mixture made by mixing 40 to 60 parts by weight of the *Huperzia serrata* powder, 90 to 110 parts by weight of the walnut powder, 90 to 110 parts by weight of the *Ginkgo biloba* leaf powder, 90 to 110 parts by weight of the lotus root powder, 40 to 60 parts by weight of the vegetable worm powder, 40 to 60 parts by weight of the *Corni fructus* powder, 90 to 110 parts by weight of the *lycium* Chinese powder, 90 to 110 parts by weight of the puer tea powder, 90 to 110 parts by weight of the Korean *angelica* root powder, 40 to 60 parts by weight of the *Saururus chinensis* (Lour.) baill powder, 40 to 60 parts by weight of the white-flowering Korean dandelion powder, and 40 to 60 parts by weight of the *perilla* powder on the basis of 100 parts by weight of the aloeswood powder and maturing the sealed mixture for six to eight days;

pouring natural water, one to three times greater than the mixture with respect to a total weight of the mixture, to the mixture whose maturing is finished and boiling the mixture at a temperature in a range of 90 to 98° C. for five to twenty minutes;

cooling and drying the mixture at an ambient temperature; and mixing the mixture with 2,500 to 3,500 parts by weight of honey on the basis of 100 parts by weight of the aloeswood.

2. The method according to claim 1, further comprising a step of, after the step of mixing the mixture with the honey, forming the mixture to a predetermined size.

\* \* \* \* \*